United States Patent
Chassot et al.

(10) Patent No.: US 6,840,965 B2
(45) Date of Patent: Jan. 11, 2005

(54) P-AMINOPHENOLS AND COLORANTS CONTAINING SAID COMPOUNDS

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 320 days.

(21) Appl. No.: 10/030,468

(22) PCT Filed: Mar. 9, 2001

(86) PCT No.: PCT/EP01/02686
§ 371 (c)(1),
(2), (4) Date: Jan. 8, 2002

(87) PCT Pub. No.: WO01/85683
PCT Pub. Date: Nov. 15, 2001

(65) Prior Publication Data
US 2003/0110577 A1 Jun. 19, 2003

(30) Foreign Application Priority Data
May 10, 2000 (DE) .......................... 100 22 828

(51) Int. Cl.[7] ................................ A61K 7/13
(52) U.S. Cl. ................ 8/405; 8/409; 8/412; 8/423; 8/408; 548/400; 549/415; 549/476; 549/478; 549/479; 549/480; 549/497; 549/502; 549/504; 549/61; 549/62; 549/63; 549/68; 549/75
(58) Field of Search ............ 8/405, 409, 412, 8/421, 423; 548/400; 549/476, 475, 478, 479, 480, 497, 502, 504, 61, 62, 63, 68, 75

(56) References Cited

FOREIGN PATENT DOCUMENTS

DE    196 07 751 A1    9/1997

OTHER PUBLICATIONS

Anna Maria Almerico et al. Polycondensed Nitrogen Heterocycles. (J. Heterocyclic Chem., 31, 193 (1994).*

* cited by examiner

*Primary Examiner*—Yogendra N. Gupta
*Assistant Examiner*—Elisa Elhilo
(74) *Attorney, Agent, or Firm*—Michael J. Striker

(57) ABSTRACT

The object of the invention are p-aminophenol derivatives of general formula (I) or physiologically tolerated, water-soluble salts thereof

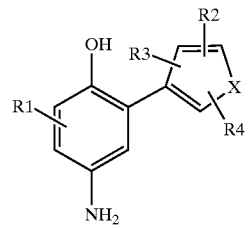

(I)

and oxidative coloring preparations based on a developer-coupler combination containing at least one p-aminophenol derivative of formula (I).

10 Claims, No Drawings

P-AMINOPHENOLS AND COLORANTS CONTAINING SAID COMPOUNDS

The invention relates to novel p-aminophenol derivatives substituted in the 2-position and to coloring preparations for dyeing keratin fibers, particularly human hair, and containing these compounds.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol and 1,4-diaminobenzene, and suitable couplers are, for example, resorcinol, 4-chlororesorcinol, 1-naphthol, 3-aminophenol, 5-amino-2-methylphenol and derivatives of m-phenylenediamine. The oxidation dyes used for dyeing human hair must meet numerous requirements in addition to that of being able to produce colorations of the desired intensity. For example, these dyes must be harmless from a toxicological and dermatological standpoint, and the obtained hair colorations must have good light fastness, resistance to permanent waving, acid fastness and rubbing fastness. In any case, however, such colorations must remain stable over a period of at least 4 to 6 weeks in the absence of exposure to light, rubbing and chemical agents. Moreover, by combination of appropriate developers and couplers, it must be possible to create a wide range of color shades. To achieve natural and especially stylish shades in the red range, p-aminophenol, alone or in admixture with other developers, in particular, is used in combination with appropriate couplers. Attempts have already been made to improve the properties of p-aminophenols by introducing substituents. In this regard, the reader is referred to German Unexamined Patent Application [DE-OS] 196 07 751 in which are also described colorants, among others, containing as developers special p-aminophenols substituted in the 2-position.

Currently known colorants, however, do not meet in all respects the requirements placed on colorants. Hence, there continues to exist a need for novel developers capable of meeting the aforesaid requirements to a very high degree.

Surprisingly, in this regard, we have now found that novel p-aminophenol derivatives of general formula (I) meet the requirements placed on developers to a particularly high degree. For example, the use of these developers in combination with most known couplers produces intense color shades that are unusually light-fast and wash-fast.

The object of the present invention are therefore p-aminophenol derivatives of general formula (I) or physiologically tolerated, water-soluble salts thereof

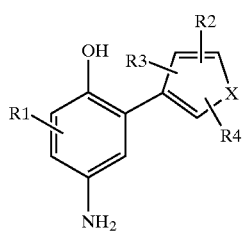

(I)

wherein
X denotes oxygen, sulfur or NR5;
R1 denotes hydrogen, a halogen atom, a $C_1$–$C_4$-alkyl group, a $C_1$–$C_4$-hydroxyalkyl group or a $C_1$–$C_4$-alkoxy group;

R2 and R4 independently of each other denote hydrogen, a hydroxyl group, a halogen atom, a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_6$-alkylamino group, a ($C_1$–$C_6$)-dialkylamino group, a —C(OH) group, a —C(O)CH$_3$ group, a —C(O)CF$_3$ group, an —Si(CH$_3$)$_3$ group, a $C_1$C$_4$-hydroxyalkyl group, a $C_3$–$C_4$-dihydroxyyalkyl group, a —CH═CHR6 group, a —(CH$_2$)$_p$—CO$_2$R7 group, a —(CH$_2$)$_p$—R8 group (with p=1,2, 3 or 4), a —C(R9)═NR10 group or a C(R11)H—NR12R13 group;

R3 denotes hydrogen, a halogen atom, a $C_1$–$C_6$-alkyl group or a —C(O)H group;

R5 denotes hydrogen, a $C_1$–$C_8$-alkyl group, a $C_1$–$C_4$-hydroxyalkyl group, a phenyl group or an acetyl group;

R6 denotes hydrogen, a hydroxyl group, a nitro group, an amino group, a —CO$_2$R7 group or a —C(O)CH$_3$ group;

R7, R9 and R11 independently of each other denote hydrogen or a $C_1$–$C_4$-alkyl group;

R8 denotes an amino group or a nitrile group;

R10, R12 and R13 independently of each other denote hydrogen, a hydroxyl group, a $C_1$–$C_4$-alkyl group, a $C_1$–$C_4$-hydroxyalkyl group, a $C_3$–$C_4$-dihydroxyalkyl group or a radical of formula (II)

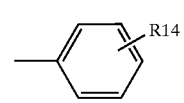

(II)

and

R14 denotes hydrogen, an amino group or a hydroxyl group.

Suitable compounds of formula (I) are, in particular: 4-amino-2-(3-thienyl)phenol; 4-amino-2-(3-furyl)phenol; 4-amino-2-(pyrrol-3-yl)phenol; 4-amino-2-(1-methyl-1H-pyrrol-3-yl)phenol; 4-amino-3-chloro-2-(3-thienyl)phenol; 4-amino-3-methyl-2-(3-thienyl)-phenol; 4-amino-5-chloro-2-(3-thienyl)phenol; 4-amino-5-methyl-2-(3-thienyl) phenol; 4-amino-6-chloro-2-(3-thienyl)phenol; 4-amino-6-methyl-2-(3-thienyl)phenol; 4-amino-2-(2-acetyl-3-thienyl) phenol; 4-amino-2-(2-chloro-3-thienyl)-phenol; 4-amino-2-(2-formyl-3-thienyl)-phenol; 4-amino-2-(2-methyl-3-thienyl)phenol; 4-amino-2-(4-acetyl-3-thienyl)phenol; 4-amino-2-(4-chloro-3-thienyl)phenol; 4-amino-2-(4-formyl-3-thienyl)phenol; 4-amino-2-(4-methyl-3-thienyl) phenol; 4-amino-2-(5-acetyl-3-thienyl)phenol; 4-amino-2-(5-chloro-3-thienyl)phenol; 4-amino-2-(5-methyl-3-thienyl) phenol or physiologically tolerated salts thereof.

Preferred compounds of formula (I) are those wherein (i) R1 denotes hydrogen and/or (ii) at least one of groups R2, R3 and R4 denotes hydrogen or a methyl group and/or (iii) X denotes sulfur or oxygen.

Particularly preferred p-aminophenol derivatives of formula (I) are 4-amino-2-(3-thienyl)phenol; 4-amino-2-(4-methyl-3-thienyl)phenol and 4-amino-2-(2-chloro-3-thienyl)phenol and physiologically tolerated salts thereof.

The compounds of formula (I) can be used as free bases and in the form of their physiologically tolerated salts of inorganic or organic acids, for example hydrochloric, sulfuric, phosphoric, acetic, propionic, lactic or citric acid.

The aminophenol derivatives of the invention of formula (I) can be prepared by synthesis methods known from the literature, for example by palladium(O)-catalyzed coupling of a substituted benzene of formula (II)

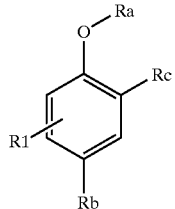

(II)

and a heteroaryl compound of formula (III)

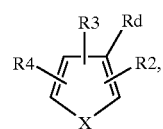

(III)

followed by elimination of the protective group, optionally followed by reduction of the nitro group, the remaining groups in formulas (II) and (III) having the following meaning:

Ra denotes a protective group—for example one described in the chapter on "Protective Groups" in Organic Synthesis, chapter 7, Wiley Interscience, 1991,—and Rb denotes an NHRa group or a nitro group; one of the two Rc and Rd groups denotes a halogen group while the other denotes a B(OH) group, and X, R1, R2, R3 and R4 have the same meanings as in formula (I).

In particular, the compounds can be used as developers in oxidative colorants and provide a wide range of different color shades extending from blond to brown, purple, violet and even blue and black.

Another object of the present invention are therefore preparations for oxidative dyeing of keratin fibers, for example hair, furs, feathers or wool, particularly human hair, based on a developer-coupler combination, containing as developer at least one p-aminophenol derivative of formula (I).

The aminophenol derivative of formula (I) is contained in the colorant of the invention in an amount from about 0.005 to 20 wt. %, an amount from about 0.01 to 5.0 and particularly from 0.1 to 2.5 wt. % being especially preferred.

Preferred couplers are 2,6-diaminopyridine, 2-amino-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-meth-ylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-amino-ethoxy)-2,4-diaminobenzene, 2-amino-1-(2-hydroxyethoxy)-4-methylaminobenzene, 2,4-diamino-phenoxyacetic acid, 3-[di-(2-hydroxyethyl)amino]aniline, 4-amino-2-di-[(2-hydroxyethyl)amino]-1-ethoxybenzene, 5-methyl-2-(1-methylethyl)phenol, 3-[(2-hydroxyethyl)amino]aniline, 3-[(2-amino-ethyl)amino]aniline, 1,3-di-(2,4-diaminophenoxy)propane, di-(2,4-diaminophenoxy)methane, 1,3-di-amino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hy-droxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although the advantageous properties of the aminophenol derivatives of formula (I) described here suggest that said derivatives should be used as the only developers, it is, of course, also possible to use the aminophenol derivatives of formula (I) together with known developers such as, for example, 1,4-diaminobenzene, 2,5-diaminotoluene, 2,5-diaminophenylethyl alcohol, N,N-bis-(2'-hydroxyethyl)-1,4-diaminobenzene, 4-aminophenol and the derivatives thereof, for example 4-amino-3-methylphenol, 4,5-diamino-1-(2-hydroxyethyl)pyrazole, or tetraaminopyrimidines.

The couplers and developers can be contained in the colorants of the invention either alone or in admixture with each other, the total amount of couplers and developers in the colorants of the invention (based on the total amount of colorant) being in all cases from about 0.005 to 20 wt. %, preferably from about 0.01 to 5.0 wt. % and particularly from 0.1 to 2.5 wt. %.

The total amount of developer-coupler combination contained in the colorants described herein is preferably from about 0.01 to 20 wt. %, an amount from about 0.02 to 10 wt. % and particularly from 0.2 to 6.0 wt. % being especially preferred. In general, the developers and couplers are used in approximately equimolor amounts. It is not disadvantageous in this respect, however, if the developers are present in a certain excess or deficiency.

Moreover, the colorants of the invention can additionally contain other dyes, for example 6-amino-2-methylphenol and 2-amino-5-methylphenol, as well as other common direct dyes, for example triphen-ylmethane dyes such as 4-[(4'-aminophenyl)-(4'-imino-2",5"-cyclohexodien-1"-ylidene)methyl]-2-methylaminobenzene monohydrochlorlde (C.I.[1] 42 510) and 4-[(4'-amino-3'-methylphenyl)-(4"-imino-3"-methyl-2",5"-cyclohexadien-1"-ylidene)methyl]-2-methylaminobenzene monohydrochloride (C.I. 42 520), aromatic nitro dyes such as 4-(2'-hydroxyethyl)

aminonitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino]-4nitrobenzene, azo dyes such as sodium 6-[(4'-aminophenyl)azo]-5-hydro-xynaphthalene-1-sulfonate (C.I. 14 805) and disperse dyes, for example 1,4-diaminoanthraquinone and 1,4,5,8-tetraaminoanthraquinone or cationic dyes.

[1]C.I.=Color Index—Translator

The colorants can contain these dyes in an amount from about 0.1 to 4.0 wt. %.

Naturally, the couplers and developers and the other dyes, as long as they are bases, can also be used in the form of physiologically tolerated salts of organic or inorganic acids, for example hydrochloric acid or sulfuric acid or—providing that they contain aromatic OH groups—in the form of salts of bases, for example as alkali metal phenoxides.

Moreover, if the colorants are to be used for coloring hair, they can contain other common cosmetic additives, for example antioxidants such as ascorbic acid, thioglycolic acid or sodium sulfite, as well as perfume oils, complexing agents, wetting agents, emulsifiers, thickeners and hair-care agents. The colorant of the invention can be a solution, particularly as an aqueous or aqueous-alcoholic solution.

A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates. alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5.0 wt. %.

Depending on the composition, the colorants of the invention can be weakly acidic, neutral or alkaline. In particular, they have a pH of about 6.5 to 11.5. Adjustment to a basic pH is preferably done with ammonia, but it can also be done with an organic amine, for example monoethanolamine and triethanolamine, or with an inorganic base such as sodium hydroxide or potassium hydroxide. Suitable for adjustment to an acidic pH are inorganic or organic acids, for example phosphoric acid, acetic acid, citric acid or tartaric acid.

For oxidative dyeing of hair, the afore-described colorants are mixed with an oxidant just before use, and the resulting mixture is applied to hair in an amount sufficient for the hair-dyeing treatment in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a p-aminophenol derivative of formula (I) as developer give hair colorations of excellent color fastness, particularly in terms of light fastness, wash fastness and rubbing fastness. As far as the dyeing properties are concerned, the hair colorants of the invention provide a wide range of different color shades from blond to brown, purple, violet and even blue and black, depending on the type and composition of the dye components. Such color shades are characterized by unusual color intensity and good color balancing of damaged and undamaged hair. The very good coloring properties of the hair colorant of the present invention also manifest themselves in that these colorants make it possible to dye graying hair, chemically not previously damaged, without any problems and with good covering power.

Preferred couplers are 2,6-diaminopyridine, 2-amino-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-meth-ylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-amino-ethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di-[(2-hydroxyethyl)amino]-1-ethoxybenzene, 5-methyl-2-(1-methylethyl)phenol,3-[(2-hydroxyethyl)amino]aniline, 3-[(2-amino-ethyl)amino]aniline,1,3-di-(2, 4-diaminophenoxy)propane, di-(2,4-diaminophenoxy)methane, 1,3-di-amino-2,4-dimethoxybenzene, 2,6-bis-(2-hydroxyethyl)aminotoluene, 4-hydroxyindole, 3-dimeth-ylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although the advantageous properties of the aminophenol derivatives of formula (I) described here suggest that said derivatives should be used as the only developers, it is, of course, also possible to use the aminophenol derivatives of formula (I) together with known developers such as, for example, 1,4-diaminobenzenes, 2,5-diaminotoluene, 2,5-diaminophenylethyl alcohol, N,N-bis-(2'-hydroxyethyl)-1,4-diaminobenzene, 4-aminophenol and the derivatives thereof, for example 4-amino-3-methylphenol, mixture was poured into 100 mL of ethyl acetate. The organic phase was extracted with dilute sodium hydroxide solution and then dried with magnesium sulfate. The solvent was distilled off in a rotary evaporator, and the residue was purified on silica gel with petroleum ether/ethyl acetate (9:1). The resulting product was heated to 50° C. in a mixture of 40 mL of ethanol and 15 mL of 2.9 M ethanolic hydrochloric acid solution. After neutralization with NaOH, the solvent was distilled off in a rotary evaporator, and the residue was purified by vacuum distillation.

This gave 4.0 g (83% of the theoretical) of 4-nitro-2-(3-thienyl)phenol with a melting point of 130° C.

D. Synthesis of 4-Amino-2-(3-thienyl)phenol Hydrochloride 3 g (13.5 mmoles) of 4-nitro-2-(3-thienyl)phenol was dissolved in 40 mL of ethanol and hydrogenated at 25° C. in the presence of 600 mg of a palladium—active carbon catalyst (10%). After the theoretically required amount of hydrogen had been absorbed, the catalyst was filtered off. Following concentration in a rotary evaporator, the reaction mixture was poured onto 20 mL of cold diethyl ether. The precipitated product was filtered off and dried.

This gave 1.95 g (75% of the theoretical) of 4-amino-2-(3-thienyl)phenol hydrochloride with a melting point of 130–132° C.

| | CHN Analysis | | | |
|---|---|---|---|---|
| ($C_{10}H_{10}NOSCl$) | % C | % H | % N | % Cl |
| Calculated | 52.75 | 4.43 | 6.15 | 15.57 |
| Found: | 52.87 | 4.75 | 5.77 | 15.10 |

EXAMPLE 2

Synthesis of 4-Amino-2-(3-heteroaryl)phenol Derivatives of Formula (I)

(General Method of Synthesis)

A. Synthesis of tert.Butyl N-(3-bromo-4-hydroxyphenyl)carbamate

A solution of 9.4 g (52.8 mmoles) of N-bromosuccinimide in 450 mL of chloroform was added dropwise to a suspension of tert.butyl N-(4-hydroxyphenyl)carbamate (10 g, 47.8 mmoles) in chloroform (100 mL) at 0° C. over a period of 2 hours. The reaction mixture was then stirred for an additional 15 min and then washed twice with water (first with 400 mL, then with 200 mL), dried with magnesium sulfate, filtered and partly evaporated. Hexane was then added to the residue with stirring which caused the formation of a precipitate. The precipitate was filtered off and washed with hexane.

This gave 9.7 g (70% of the theoretical) of tert.butyl N-(3-bromo-4-hydroxyphenyl)carbamate.

$^1$H-NMR (300 MHz, $CDCl_3$):δ=7.68(br s, 1H); 7.05 (dd, 1H); 6.93 (d, 1H); 6.37 (br s; 2H); 5.39 (s, 1H); 1.51 (s, 9H).

B. Synthesis of tert.Butyl N-(3-Bromo-4-ethoxymethoxyphenyl)carbamate 0.76 g (17.4 mmoles) of a sodium hydride dispersion (55% in oil) was added portionwise at 0° C. to a solution of 5 g (17.4 mmoles) of tert.butyl N-(3-bromo-4-hydroxyphenyl)carbamate in 60 mL of tetrahydrofuran. The mixture was then stirred for 50 min at 0° C. after which 1.83 g (19.4 mmoles) of chloromethyl ethyl ether was added. The mixture was stirred for an additional hour at 0° C. It was then poured onto ice and extracted with ethyl acetate, and the organic phase was washed with a saturated sodium chloride solution, dried over $Na_2SO_4$, filtered and concentrated. The residue was purified on silica gel with petroleum ether/ethyl acetate (9:1).

This gave 4.8 g (80% of the theoretical) of tert.butyl N-(3-bromo-4-hydroxyphenyl)carbamate.

$^1$H-NMR (300 MHz, $CDCl_3$):δ=7.66 (d, 1H); 7.16 (dd, 1H); 7.08 (d, 1H); 5.23 (s, 2H); 3.77 (q, 2H); 1.51 (s, 9H); 1.22 (t, 3H).

C. Synthesis of tert.Butyl N-{4-ethoxymethoxy-3-(4,4,5,5-tetramethyl[1,3,2]dioxaborolan-2-yl)phenyl}carbamate 210 mL of degassed dioxane was added under argon to a mixture of 7.0 g (20.2 mmoles) of tert.butyl N-(3-bromo-4-ethoxymethoxyphenyl)carbamate, 12.8 g (50.6 mmoles) of diboronpinacol ester, 2.0 g (2.9 mmoles) of dichloro-1,1'-bis-[diphenylphosphino)ferrocene]palladium [$PdCl_2$(dppf)] and 6.2 g (63.2 mmoles) of potassium acetate. The mixture was then stirred 26 hours at 80° C. after which to it was added a mixture of 4.2 g (16.9 mmoles) of diboronpinacol ester and 0.7 g (0.95 mmole) of $PdCl_2$(dppf). The mixture was then stirred at 80° C. for an additional 14 hours. The reaction mixture was then poured into water and extracted with ethyl acetate, and the organic phase was washed with a saturated sodium chloride solution, dried over $Na_2SO_4$ and after filtration concentrated. Finally, the crude product was purified on deactivated silica gel with hexane/ethyl acetate.

This gave 5.30 g (61% of the theoretical) of tert.butyl N-{4-ethoxymethoxy-3-(4,4,5,5-tetramethyl-[1,3,2] dioxaborolan-2yl)phenyl}carbamate.

D. Synthesis of 4-Amino-2-(3-heteroaryl)phenols 0.036 g (0.1 mmole) of tert.butyl N-[4-ethoxymethoxy-3-(4,4,5,5-tetramethyl[1,3,2]dioxaborolan-2-yl)phenyl]carbamate and 0.013 mole of the corresponding bromo derivative were dissolved in 70 mL of 1,2-dimethoxyethane under argon. Then, 0.5 g (0.5 mmole) of tetrakis-(triphenylphosphine)palladium and 13 mL of a 2 N potassium carbonate solution were added, and the reaction mixture was heated to 80° C. At the end of the reaction, the reaction mixture was poured into 100 mL of ethyl acetate, and the organic phase was extracted with diluted sodium hydroxide solution and then dried with magnesium sulfate. The solvent was distilled off in a rotary evaporator, and the residue was purified on silica gel with petroleum ether/ethyl acetate (9:1). The resulting product was heated to 50° C. in 40 mL of ethanol. To prepare the hydrochloride, 15 mL of 2.9 M ethanolic hydrochloric acid was then added dropwise. The precipitate was filtered off, washed twice with 10 mL of ethanol and dried.

a. 4-Amino-2-(4-methylthiophen-3-yl)phenol hydrochloride

| | |
|---|---|
| Bromo derivative used: | 3-bromo-4-methylthiophene |
| Yield: | 0.02 g (90% of the theoretical) |
| Mass spectrum: | MH$^+$ 206 (100) | b. 4-Amino-2-(2-chlorothiophen-3-yl)phenol hydrochloride

| | |
|---|---|
| Bromo derivative used: | 3-bromo-2-chlorothiophene |
| Yield: | 0.025 g (93% of the theoretical) |
| Mass spectrum: | M$^+$ 225 (100) [sic - Translator] | c. 4-Amino-2-furan-3-ylphenol hydrochloride

| | |
|---|---|
| Bromo derivative used: | 3-bromofuran |
| Yield: | 0.012 g (53% of the theoretical) |
| Mass spectrum: | MH$^+$ 176 (100) |

EXAMPLES 3 TO 18

Hair Colorants

Hair colorant solutions having the following composition were prepared:

| | | |
|---|---|---|
| 1.25 | mmoles | of developer of formula (I) according to Table 1 |
| 1.25 | mmoles | of coupler according to Table 1 |
| 1.0 | g | of potassium oleate (8% aqueous solution) |
| 1.0 | g | of ammonia (22% aqueous solution) |
| 1.0 | g | of ethanol |
| 0.3 | g | of ascorbic acid |
| to 100.0 | g | water |

Immediately before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. The coloring results are presented in Table 1.

TABLE 1

| Example/ shade | Developer of Formula (I) | Coupler |
|---|---|---|
| 3 light-blond | 4-amino-2-(3-thienyl)phenol | 1,3-dihydroxybenzene |
| 4 light-blond | 4-amino-2-(5-methylthiophen-3-yl)phenol hydrochloride | 1,3-dihydroxybenzene |
| 5 light-blond | 4-amino-2-(5-nitrothiophen-3-yl)phenol hydrochloride | 1,3-dihydroxybenzene |
| 6 light-blond | 4-amino-2-furan-3-ylphenol hydrochloride | 1,3-dihydroxybenzene |
| 7 red-violet | 4-amino-2-(3-thienyl)phenol | 1,3-diamino-4-(2'-hydroxy-ethoxy)benzene sulfate |
| 8 red-violet | 4-amino-2-(5-methylthiophen-3-yl)phenol hydrochloride | 1,3-diamino-4-(2'-hydroxy-ethoxy)benzene sulfate |
| 9 red-violet | 4-amino-2-(5-nitrothiophen-3-yl)phenol hydrochloride | 1,3-diamino-4-(2'-hydroxy-ethoxy)benzene sulfate |
| 10 red-violet | 4-amino-2-furan-3-ylphenol hydrochloride | 1,3-diamino-4-(2'-hydroxy-ethoxy)benzene sulfate |
| 11 red-orange | 4-amino-2-(3-thienyl)phenol | 5-amino-2-methylphenol |
| 12 red-orange | 4-amino-2-(5-methylthiophen-3-yl)phenol hydrochloride | 5-amino-2-methylphenol |
| 13 red-orange | 4-amino-2-(5-nitrothiophen-3-yl)phenol hydrochloride | 5-amino-2-methylphenol |
| 14 red-orange | 4-amino-2-furan-3-ylphenol hydrochloride | 5-amino-2-methylphenol |
| 15 violet | 4-amino-2-(3-thienyl)phenol | 1-naphthol |

TABLE 1-continued

| Example/ shade | Developer of Formula (I) | Coupler |
|---|---|---|
| 16 violet | 4-amino-2-(5-methylthiophen-3-yl)phenol hydrochloride | 1-naphthol |
| 17 violet | 4-amino-2-(5-nitrothiophen-3-yl)phenol hydrochloride | 1-naphthol |
| 18 violet | 4-amino-2-furan-3-ylphenol hydrochloride | 1-naphthol |

EXAMPLES 19 TO 34

Hair Colorants

Hair colorant solutions having the following composition were prepared:

| | | |
|---|---|---|
| X | g | of developer E1 of formula (I) according to Table 3 |
| U | g | of developer E2 to E9 according to Table 3 |
| Y | g | of coupler K11 to K36 according to Table 4 |
| Z | g | of direct dye D1 to D3 according to Table 2 |
| 10.0 | g | of potassium oleate (8% aqueous solution) |
| 10.0 | g | of ammonia (22% aqueous solution) |
| 10.0 | g | of ethanol |
| 0.3 | g | of ascorbic acid |
| to 100.0 | g | water |

Immediately before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. The coloring results are presented in Table 5.

EXAMPLES 35 TO 40

Hair Colorants

Dye carriers in cream form and having the following composition were prepared:

| | | |
|---|---|---|
| X | g | of developer E1 of formula (I) according to Table 3 |
| Y | g | of coupler K11 to K36 according to Table 4 |
| Z | g | of direct dye D1 to D3 according to Table 2 |
| 15.0 | g | of cetyl alcohol |
| 0.3 | g | of ascorbic acid |
| 3.5 | g | of sodium lauryl alcohol diethylene glycol ether sulfate, 28% aqueous solution |
| 3.0 | g | of ammonia, 22% aqueous solution |
| 0.3 | g | of sodium sulfite, anhydrous |
| to 100 | g | water |

Immediately before use, 30 g of the foregoing coloring cream was mixed with 30 g of a 6% aqueous solution of hydrogen peroxide. The mixture was then applied to the hair. After an exposure time of 30 min, the hair was rinsed with water, washed with a commercial shampoo and dried. The coloring results are presented in the following Table 6.

TABLE 2

Direct Dyes

| | |
|---|---|
| D1 | 2,6-Diamino-3-[(pyridin-3-yl)azo]pyridine |
| D2 | 6-Chloro-2-ethylamino-4-nitrophenol |
| D3 | 2-Amino-6-chloro-4-nitrophenol |

TABLE 3

Developers

| | |
|---|---|
| E1 | 4-Amino-2-(3-thienyl)phenol hydrochloride (according to Example 1D) |
| E2 | 1,4-Diaminobenzene |
| E3 | 2,5-Diaminophenylethanol sulfate |
| E4 | 3-Methyl-4-aminophenol |
| E5 | 4-Amino-2-aminomethylphenol dihydrochloride |
| E6 | 4-Aminophenol |
| E7 | N,N,-Bis-(2'-hydroxyethyl)-p-phenylenediamine sulfate |
| E8 | 4,5-Diamino-1-(2'-hydroxyethyl)pyrazole sulfate |
| E9 | 2,5-Diaminotoluene sulfate |

TABLE 4

Couplers

| | |
|---|---|
| K11 | 1,3-Diaminobenzene |
| K12 | 2-Amino-4-(2'-hydroxyethyl)aminoanisole sulfate |
| K13 | 1,3-Diamino-4-(2'-hydroxyethoxy)benzene sulfate |
| K14 | 2,4-Diamino-5-fluorotoluene sulfate |
| K15 | 3-Amino-2-methylamino-6-methoxypyridine |
| K16 | 3,5-Diamino-2,6-dimethoxypyridine dihydrochloride |
| K17 | 2,4-Diamino-5-ethoxytoluene sulfate |
| K18 | N-(3-Dimethylamino)phenylurea |
| K19 | 1,3-Bis-(2,4-diaminophenoxy)propane tetrahydrochloride |
| K21 | 3-Aminophenol |
| K22 | 5-Amino-2-methylphenol |
| K23 | 3-Amino-2-chloro-6-methylphenol |
| K24 | 5-Amino-4-fluoro-2-methylphenol sulfate |
| K25 | 1-Naphthol |
| K26 | 1-Acetoxy-2-methylnaphthalene |
| K31 | 1,3-Dihydroxybenzene |
| K32 | 2-Methyl-1,3-dihydroxybenzene |
| K33 | 1-Chloro-2,4-dihydroxybenzene |
| K34 | 4-(2'-Hydroxyethyl)amino-1,2-methylenedioxybenzene hydrochloride |
| K35 | 3,4-Methylenedioxyphenol |
| K36 | 2-Amino-5-methylphenol |

TABLE 5

Hair Colorants

| | Example | | | | | |
|---|---|---|---|---|---|---|
| Dye | 19 | 20 | 21 | 22 | 23 | 24 |
| | (Quantity of dye in grams) | | | | | |
| E1 | 0.096 | 0.24 | 0.3 | 0.04 | 0.01 | 0.7 |
| E2 | | | 0.9 | | | |
| E5 | | | | | | |
| E6 | | | | | | |
| E9 | | | | | 0.096 | 1.8 |
| K12 | | | | 0.01 | | |
| K18 | | | | | | 0.03 |
| K21 | | | | 0.02 | | 0.06 |
| K22 | 0.08 | 0.2 | 0.25 | 0.056 | | 0.58 |
| K25 | | | | 0.03 | | |
| K31 | | | | 0.2 | | 0.8 |
| K32 | | 0.03 | 0.05 | 0.316 | | |
| K35 | 0.018 | | | | | |
| K36 | | 0.03 | 0.05 | 0.01 | | |
| K26 | | | | | | |

TABLE 5-continued

Hair Colorants

| | | | | 0.01 | | |
|---|---|---|---|---|---|---|
| D1 | | | | 0.01 | | |
| D3 | 0.04 | 0.06 | 0.025 | | | |
| Shade | light-blond copper-gold | coppe gold | light copper tones | purple-brown | silver-blond | dark mahogany |

| | Example | | | | | |
|---|---|---|---|---|---|---|
| Dye | 25 | 26 | 27 | 28 | 29 | 30 |
| | (Quantity of dye in grams) | | | | | |
| E1 | 0.01 | 0.6 | 1 | 0.2 | 0.8 | 0.6 |
| E2 | 2.0 | | | 1.9 | | |
| E3 | | 0.05 | | | | |
| E8 | | | 1 | | | |
| E9 | | | | | 1 | 0.7 |
| K12 | | | 1.1 | | | |
| K13 | 0.07 | | | | | 0.8 |
| K16 | | | | | | 1.0 |
| K17 | | | 1.1 | | | |
| K18 | | | | 1.25 | | |
| K21 | 0.4 | | | 0.28 | | |
| K22 | 0.08 | 0.5 | | | | |
| K25 | | | | | 0.8 | |
| K31 | 0.8 | | | | | |
| K32 | | 0.03 | | | | |
| K33 | | | | | 0.75 | |
| K36 | | 0.03 | | | | |
| D1 | | 0.25 | | | | |
| D3 | | 0.15 | | | | |
| Shade | black-brown | orange | blue-violet | blue-red | pink | Bordeaux tones |

| | Example | | | |
|---|---|---|---|---|
| Dye | 31 | 32 | 33 | 34 |
| | (Quantity of dye in grams) | | | |
| E1 | 0.01 | 0.01 | 0.05 | 0.6 |
| E3 | 1.4 | 4.5 | | |
| E5 | | | | 0.25 |
| E6 | | | 0.1 | |
| E8 | | 0.8 | 0.5 | 0.01 |
| E9 | 2.5 | | | |
| K12 | 0.6 | | | |
| K13 | 0.2 | | | 0.8 |
| K14 | | 0.25 | | |
| K16 | 0.01 | | | |
| K18 | | | | 1.25 |
| K19 | 0.8 | | | |
| K21 | 0.3 | | | 0.28 |
| K22 | | 5.0 | | |
| K25 | | 0.4 | | |
| K23 | | | 0.6 | |
| K31 | 1.1 | | | |
| K32 | | | | 0.33 |
| K36 | | | 0.19 | |
| D2 | | | 0.5 | |
| Shade | black | red-violet | red-orange | warm yellow |

In material reproduced from the German document, commas denote decimal points - Translator

Table 6

Hair Colorants

| | Example | | | | | |
|---|---|---|---|---|---|---|
| Dye | 35 | 36 | 37 | 38 | 39 | 40 |
| | (Quantity of dye in grams) | | | | | |
| E1 | 0.1 | 0.2 | 0.01 | 2.0 | 0.5 | 0.7 |

Table 6-continued

Hair Colorants

| Dye | 35 | 36 | 37 | 38 | 39 | 40 |
|---|---|---|---|---|---|---|
| | (Quantity of dye in grams) | | | | | |
| E4 | | | | | | 1.6 |
| E8 | | | | 0.25 | 0.8 | 0.2 |
| E9 | 3.2 | 1.71 | 0.02 | | | 1.8 |
| K13 | 0.23 | 0.1 | | | 1.3 | |
| K14 | 0.2 | | | | | |
| K16 | | | 0.015 | | | |
| K21 | 0.4 | 0.8 | | | 0.02 | |
| K22 | 0.08 | | 0.25 | 1.8 | | 4.5 |
| K23 | | 0.2 | | | 0.03 | |
| K31 | 1.05 | 0.135 | 0.02 | 0.25 | | 0.8 |
| K25 | | | | | | 0.55 |
| K26 | | | 0.03 | | | |
| K19 | | | | | 1.7 | |
| K36 | | 0.27 | | | | |
| D2 | | 0.01 | | | | |
| Shade | dark-brown | chocolate brown | silver blond | orange tones | blue-violet | red-violet |

Unless otherwise indicated, all percentages given in the present patent application are by weight.

What is claimed is:

1. p-Aminophenol derivatives of general formula (I) or physiologically tolerated, water-soluble salts thereof

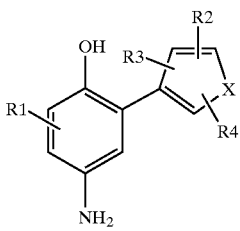

(I)

wherein

X denotes oxygen or sulfur,

R1 denotes hydrogen, a halogen atom, a $C_1$–$C_4$-alkyl group, a $C_1$–$C_4$-hydroxyalkyl group or a $C_1$–$C_4$-alkoxy group;

R2 and R4 independently of each other denote hydrogen, a hydroxyl group, a halogen atom, a cyano group, a $C_1$–$C_4$-alkoxy group, a $C_1$–$C_6$-alkyl group, a $C_1$–$C_4$-alkyl thioether group, a mercapto group, a nitro group, an amino group, a $C_1$–$C_6$-alkylamino group, a ($C_1$–$C_8$)-dialkylamino group, a —C(OH) group, a —C(O)CH$_3$ group, a —C(O)CF$_3$ group, an —Si(CH$_3$)$_3$ group, a $C_1$–$C_4$-hydroxyalkyl group, a $C_3$–$C_4$-dihy-droxyalkyl group, a —CH=CHR6 group, a —(CH$_2$)$_p$—CO$_2$R7 group or a —(CH$_2$)$_p$—R8 group (with p=1,2, 3 or 4), a —C(R9)=NR10 group or a C(R11)H-NR12R13 group;

R3 denotes hydrogen, a halogen atom, a $C_1$–$C_8$-alkyl group or a —C(O)H group;

R6 denotes hydrogen, a hydroxyl group, a nitro group, an amino group, a —CO$_2$R7 group or a —C(O)CH$_3$ group;

R7, R9 and R11 independently of each other denote hydrogen or a $C_1$–$C_4$-alkyl group;

R8 denotes an amino group or a nitrile group;

R10, R12 and R13 independently of each other denote hydrogen, a hydroxyl group, a $C_1$–$C_4$-alkyl group, a $C_1$–$C_4$-hydroxyalkyl group, a $C_3$–$C_4$-dihydroxyalkyl group or a radical of formula (II)

(II)

and

R14 denotes hydrogen, an amino group or a hydroxyl group.

2. p-Aminophenol derivative according to claim 1, characterized in that it is selected from the (group consisting of 4-amino-2-(3-thienyl)phenol; 4-amino-2-(3-furyl)phenol; 4-amino-2-(pyrrol-3-yl)-phenol; 4-amino-2-(1-methyl-1H-pyrrol-3-yl)phenol; 4-amino-3-chloro-2-(3-thienyl)phenol, 4-amino-3-methyl-2-(3-thienyl)phenol; 4-amino-5-chloro-2-(3-thienyl)phenol; 4-amino-5-methyl-2-(3-thienyl)-phenol; 4-amino-6-chloro-2-(3-thienyl)phenol; 4-amino-6-methyl-2-(3-thienyl)phenol; 4-amino-2-(2-acetyl-3-thienyl)phenol; 4-amino-2-(2-chloro-3-thienyl)phenol; 4-amino-2-(2-formyl-3-thienyl)-phenol; 4-amino-2-(2-methyl-3-thienyl)phenol; 4-amino-2-(4-acetyl-3-thienyl)phenol; 4-amino-2-(4-chloro-3-thienyl)phenol; 4-amino-2-(4-formyl-3-thienyl)phenol; 4-amino-2-(4-methyl-3-thienyl) phenol; 4-amino-2-(5-acetyl-3-thienyl)phenol; 4-amino-2-(5-chloro-3-thienyl)phenol; 4-amino-2-(5-methyl-3-thienyl) phenol and the physiologically tolerated salts thereof.

3. p-Aminophenol derivative according to claim 1, characterized in that in formula (I) (i) R1 denotes hydrogen and/or (ii) at least one of groups R2, R3 and R4 denotes hydrogen or a methyl group and/or (iii) X denotes sulfur or oxygen.

4. p-Aminophenol derivative according to claim 1, characterized in that it is selected from the group consisting of 4-amino-2-(3-thienyl)phenol; 4-amino-2-(4-methyl-3-thienyl)phenol and 4-amino-2-(2-chloro-3-thienyl)phenol and physiologically tolerated salts thereof.

5. Preparation for oxidative dyeing of keratin fibers based on a developer-coupler combination, characterized in that said preparation contains as the developer at least one p-aminophenol derivative of formula (I) according to claim 1.

6. Preparation according to claim 5, characterized in that it contains the p-aminophenol derivative of formula (I) in an amount from 0.005 to 20.0 wt.%.

7. Preparation according to claim 5, characterized in that the coupler is selected from the group consisting of 2,6-diaminopyridine, 2-amino-4-[(2-hydroxyethyl)amino] anisole, 2,4-diamino-1-flouro-5-methylbenzene, 2,4-diamino-1-methoxy-5-methylbenzene, 2,4-diamino-1-ethoxy-5-methyl-benezene, 2,4-diamino-1-(2-hydroxyethoxy)-5-methylbenzene, 2,4-di[(2-hydroxyethyl)amino]-1,5-dimeth-oxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di-[2-hydroxyethyl)amino]-1-ethoxybenzene, 5-methyl-2-(1-methylethyl)phenol, 3-[(2-hydroxyethyl)amino]aniline, 3[(2-aminoethyl)amino]aniline, 1,3-di-(2,4-diaminophenoxy)propane, di-(2,4-diaminophenoxy) methane, 1,3-diamino-2,4-dimethoxy-benzene, 2,6-bis-(2- hydroxyethyl)aminotoluene, 4-hydroxyindole, 3-dimethylaminophenol, 3-diethyl-aminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydro-xyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihy-droxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

8. Preparation according to claim 5, characterized in that it contains the developers and couplers in a total amount of 0.005 to 20 wt. %, based on the total amount of colorant.

9. Preparation according to claim 5, characterized in that it contains additionally at least one direct dye.

10. Preparation according to claim 5, characterized in that it is a hair colorant.

* * * * *